US006925880B1

(12) United States Patent  (10) Patent No.: US 6,925,880 B1
Roberts  (45) Date of Patent: Aug. 9, 2005

(54) APPARATUS AND METHOD FOR MEASURING THE ACOUSTIC PROPERTIES OF A MEMBRANOPHONE

(76) Inventor: John H. Roberts, P.O. Box 297, Hickory, MS (US) 39332

( * ) Notice: Subject to any disclaimer, the term of this patent is extended or adjusted under 35 U.S.C. 154(b) by 0 days.

(21) Appl. No.: 10/714,747

(22) Filed: Nov. 17, 2003

(51) Int. Cl.⁷ .................. G01N 29/04; H04R 29/00
(52) U.S. Cl. .............. 73/587; 73/579; 73/602; 381/58
(58) Field of Search ............ 73/587, 579, 597, 73/598, 602; 84/411 R, 723; 381/58, 59

(56) References Cited

U.S. PATENT DOCUMENTS

| | | | | |
|---|---|---|---|---|
| 4,230,013 A | * | 10/1980 | Wellings ............... | 84/733 |
| 4,287,806 A | | 9/1981 | Neary ................... | 86/658 |
| 4,480,473 A | * | 11/1984 | Varterasian .......... | 73/596 |
| 4,899,636 A | * | 2/1990 | Chiba et al. .......... | 84/454 |
| 5,251,264 A | * | 10/1993 | Tichy ................... | 381/173 |
| 5,533,405 A | | 7/1996 | Hoshino ............... | 37/189 |
| 5,583,307 A | * | 12/1996 | Tobia, Jr. ............. | 84/411 R |
| 5,892,168 A | * | 4/1999 | Donohoe .............. | 84/411 M |
| 5,902,252 A | * | 5/1999 | Hohlfeld et al. ..... | 600/559 |
| 6,121,528 A | * | 9/2000 | May ..................... | 84/411 R |
| 6,525,249 B1 | * | 2/2003 | Suenaga ............... | 84/411 R |
| 6,784,352 B2 | * | 8/2004 | Suenaga ............... | 84/411 R |
| 6,794,569 B2 | * | 9/2004 | Kamijima et al. ... | 84/746 |

* cited by examiner

*Primary Examiner*—Hezron Williams
*Assistant Examiner*—Jacques M. Saint-Surin
(74) *Attorney, Agent, or Firm*—Stout, Uxa, Buyan & Mullins, LLP (57) ABSTRACT

Apparatus and method of measuring acoustic properties of a drumhead of a drum are disclosed. The acoustic properties are measured by exciting the drumhead with a source of energy and detecting the acoustic energy emitted by the drumhead. The acoustic energy emitted by the drumhead may be measured using a microphone or other acoustic sensor. The use of multiple energy sources provides isolation of acoustic energy and allows measurement of local resonance of the drumhead.

21 Claims, 6 Drawing Sheets

APPARATUS AND METHOD FOR MEASURING THE ACOUSTIC PROPERTIES OF A MEMBRANOPHONE

BACKGROUND OF THE INVENTION

1. Field of the Invention

This invention generally relates to an apparatus and a method for measuring the acoustic properties, such as the resonant tuning, of a membranophone, such as a drumhead of a drum. More specifically, this invention relates to an apparatus and a method for measuring or monitoring the sounds made by a drum at the time the tension of a drumhead of the drum is being adjusted.

2. Description of Related Art

Musical performance drums have one or more beatable membranes which are called drumheads. The drumhead is mounted on the upper edge, and optionally the lower edge, of the generally cylindrical drum body. A drumhead tightening hoop or ring is typically placed on the outer peripheral edge of a drumhead around the drum body. Typically, a plurality of tightening bolts are screwed to respective lug nuts which have been arranged at spaced intervals around the outer periphery of the drum body. Usually, the tightening bolts and lug nuts are equally spaced around the periphery of the drum body. The drumhead tightening hoop may be compressively tightened over the drum body using the tightening bolts and lug nuts to fix the drumhead to the drum body. A tuning key or wrench tightens the drumhead by selectively tightening each tightening bolt and its lug nut. Generally, the drumhead is evenly stretched over the entire drum body edge, such as the upper and/or lower edge, prior to being used, such as in a musical performance.

Obtaining a relatively specific or precise amount of stretching of the drumhead is important for the performance of the drum in general. For example, stretching a drumhead too tightly may lead to durability problems. Such durability problems may be attributed to the tension of the drumhead exceeding the range of elastic deformation of the material from which the drumhead is made. For example, many drumheads include a polyester film. By excessively tightening the drumhead, the range of elastic deformation may be exceeded, or the tension of the drumhead may be greater than the material's (e.g., polyester film) yield point, thereby causing deformation or rupture of the drumhead. Alternatively, any drumhead attached with inadequate tension may not maintain continuous contact with the edge of the drum body when struck by a beater and thus, the drum will generate non-musical sounds. When the drumhead is tensioned between these extremes (e.g., too tight and too loose) and the drumhead is struck by a beater, the drum typically resonates at multiple frequencies.

Circular drumheads typically have multiple resonances. The first or lower primary frequency involves the entire drumhead and is a product of the average drumhead tension. Influenced by the geometry of a circular drumhead, higher frequency modes typically follow sundry paths across and around the drumhead. Due to flexure of the drumhead tightening hoop, these higher frequency vibratory modes are also often influenced by the local tension associated with each tightening bolt/lug nut pair. If the drumhead is not precisely tensioned at every tightening bolt/lug nut pair, the overtone vibratory modes (e.g., higher frequency modes) will be diffuse when the drumhead is struck, thereby resulting in diminished tonal purity, and reduced sustainability.

In the past, to tune the drumhead and to clear the drumhead of these non-musical overtones, the drumhead was lightly beaten with a stick in the vicinity of each tightening bolt/lug nut pair. The prominent overtone sound which was generated was compared with the sound generated by beating in the vicinity of the other tightening bolt/lug nut pairs so that each tightening bolt/lug nut pair might be adjusted with the tuning key so as to eliminate the difference between the higher and the lower tensioned pairs. An alternate approach was to apply pressure with a finger to the drumhead at or near its center to create a node or point of no vibration. When lightly beaten with a stick at points midway between the center and each tightening bolt/lug nut pair radially in line with that pair, the lower primary resonance was suppressed and the overtone sound related to the tension from that tightening bolt/lug nut pair became more apparent.

Unfortunately, while performing this adjusting operation, a person typically must listen to the sounds generated by striking the drumhead and rely upon short term tonal memory of the frequencies being generated. Tuning success using this method requires accurately striking the drumhead at specific locations with consistent force, while precisely remembering the exact tone generated by previous tests. In addition, minor changes in tension applied to the drumhead to dampen the primary vibration mode in the alternate tuning approach will likely alter the apparent tension of the drumhead and introduce adjustment errors. Tension errors from adjacent tightening bolt/lug nut pairs may also interact and complicate this tuning effort. The skill and patience to complete such adjustments using these methods are typically beyond the ability of many drum owners who routinely must perform with poorly tuned drumheads. To address these problems, mechanical tuning aids have been developed to assist drum owners in this difficult task.

One mechanical aid is disclosed in U.S. Pat. No. 4,287,806. The device disclosed therein involves use of a torque indicator on each tightening bolt to facilitate consistent lug tension. While this can be an improvement over manual tuning, the relationship between tightening bolt torque and drumhead tension can be degraded by thread quality and condition of the tightening bolt and lug nut. In addition, any deviations from flatness in the drumhead tensioning hoop and drum shell knife edge will likely introduce distortions in the tension applied to the drumhead. The success of this approach requires very accurate drum manufacturing tolerances and the fitness of the mechanical hardware.

A second mechanical device is disclosed in U.S. Pat. No. 5,533,405. The device disclosed therein attempts to overcome some of the limitations associated with the device disclosed in U.S. Pat. No. 4,287,806 by applying a known force directly to a point on the drumhead and measuring the deflection of the drumhead. The amount of this deflection may be representative of the mechanical properties of the drumhead material, drumhead material thickness, and/or tension at that location. This is an improvement over U.S. Pat. No. 4,287,806 but still suffers inaccuracies from mechanical or fabrication variations in the drum/drumhead system, and requires precise placement on the drumhead for reliable measurements.

One weakness common to the approaches disclosed in U.S. Pat. Nos. 4,287,806 and 5,533,405 is that the measurement methods are indirect. The methods and devices do not actually measure the vibration of the excited drum/drumhead system but measure mechanical parameters that influence this vibration and rely upon other unmeasured parameters to be ideal or held to very precise manufacturing tolerances. If any of these unmeasured parameters deviate the resultant drum tuning accuracy will deteriorate.

In addition, external frequency references such as tuning forks have also been used in orchestral settings to aid in average tuning of drumheads but do not offer any specific relief from the problem of balancing relative tension of individual tension bolts/lug nut pairs, as discussed herein.

SUMMARY OF THE INVENTION

The present invention herein disclosed relates to an apparatus and a method for measuring or determining the acoustic properties of a drumhead of a drum, as discussed herein. The invention attempts to address the above described problems associated with existing devices and methods, among other things. The apparatus and method disclosed herein involve isolating and measuring the drumhead resonance associated with the tension of the drumhead at an area in proximity to an individual tightening bolt/lug nut pair. Measuring and adjusting all of the tightening bolt/lug nut pairs to the same resonant frequency delivers a degree of tuning precision not previously possible. In addition, the apparatus and method provide a accurate and reliable measurement of the acoustic properties of a drumhead that are not available with existing devices and methods.

In one embodiment, an apparatus for measuring acoustic properties of a drumhead of a drum comprises an energy source positioned relative to the drum to cause the drumhead to vibrate when energy is delivered from the energy source towards the drumhead; and an acoustic sensor positioned relative to the drumhead to receive acoustic energy therefrom, and coupled to a meter configured to display information corresponding to the acoustic properties of the drumhead.

In another embodiment, an apparatus for measuring acoustic properties of a drumhead of a drum comprises an acoustic energy source positioned relative to the drum to provide acoustic energy to the drumhead; and an acoustic energy sensor positioned to receive acoustic energy from the drumhead and configured to generate an output signal corresponding to the acoustic energy received by the acoustic sensor.

A method as disclosed herein comprises applying energy to a surface of the drumhead to cause the drumhead to emit acoustic energy therefrom. Acoustic energy emitted from the drumhead is received using an acoustic sensor positioned away from the surface of the drumhead. The acoustic energy received from the acoustic sensor is converted into a signal corresponding to an acoustic property of the drumhead.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention.

Additional advantages and aspects of the present invention are apparent in the following detailed description and claims.

DETAILED DESCRIPTION OF THE PRESENTLY PREFERRED EMBODIMENTS

Apparatus and method for measuring or determining the acoustic properties of a drumhead of a drum are disclosed. The apparatus and method disclosed herein provide energy to a surface of the drumhead. The energy provided to the surface causes the drumhead to vibrate and emit acoustic energy. The acoustic energy is received by one or more acoustic sensors, and is transformed into a signal that corresponds to the acoustic energy. The signal may then be read or viewed by the tuner of the drum. Thus, the apparatus and method attempt to provide enhanced measurement of the acoustic properties of the drum by measuring the acoustic energy that is emitted from the drumhead under controlled conditions.

In general, an apparatus, as disclosed herein, comprises an energy source that is configured to provide energy to the drum. The energy is directed towards the drumhead of the drum to cause the drumhead to vibrate. Thus, the energy may be mechanical or acoustic. In one embodiment disclosed herein, and discussed in more detail with respect to the figures, the energy is acoustic energy provided by an acoustic energy source. Typically, the energy source provides a predetermined or controlled amount of energy to the drumhead so that the acoustic properties of the drumhead can be accurately measured. In preferred embodiments, the energy source provides energy to the drum without providing a physical contact with a drumhead. An acoustic energy source may include one or more speakers which are configured to emit a predetermined or controlled amount of acoustic energy to the drumhead. The energy source of the apparatus may include a transducer that is configured to convert electrical energy into either mechanical or acoustic energy. Thus, the energy provided to the drumhead may originate as electrical energy, be converted to mechanical or acoustic energy and then directed towards the drumhead to cause the drumhead to vibrate. The drum/shell/head combination of a typical drum forms a highly resonant system that can selectively enhance some frequencies with respect to others. Such behavior can return a lower distortion sine wave than the drumhead initially receives. The drumhead can generate multiple resonances. One important distinction about drums regarding these overtones is that the overtones are not simple multiples (octaves) like other musical instruments. Due to the physics of vibration across and around the drumhead, overtones occur at non-integer multiples.

The apparatus also includes an acoustic sensor. The acoustic sensor is typically positioned relative to the drumhead to receive acoustic energy emitted from the drumhead due to the energy delivered from the energy source, described above. The acoustic sensor may be coupled to a meter that is configured to display information corresponding to the acoustic properties of the drumhead. The acoustic sensor may also include a transducer. The acoustic sensor transducer will typically convert the acoustic energy received from the drumhead into an electrical signal, such as a voltage. The electrical signal can then be used by the meter to provide a measurement corresponding to the acoustic properties of the drumhead. For example, by monitoring local maxima in the amplitude of the acoustic energy radiated from the drumhead as the frequency of the energy source is varied, the precise frequency of the important resonance can be identified. Alternately the drumhead can be excited with a fixed target frequency and the amplitude for a maxima or resonance can be monitored while adjusting the drumhead tension. Or, the phase relationships of the resulting signals may be used to tune the drumhead.

As indicated herein, the energy source of the apparatus may comprise an acoustic energy source or a mechanical energy source. In one embodiment, and as discussed in more detail with respect to the accompanying figures, the energy source comprises an acoustic energy source coupled to at least one speaker. Any conventional speaker may be used so long as it is configured to emit acoustic energy within an appropriate frequency range. Typically, when acoustic energy is used to activate the drumhead, the energy source is spaced away from the drumhead. Thus, the drumhead can be activated or excited using only acoustic energy emitted from the acoustic energy source. In certain embodiments disclosed herein, a plurality of energy sources may be provided with the apparatus. In one embodiment, the apparatus comprises two energy sources spaced apart by a distance. By using more than one energy source, it is possible to achieve improved isolation of the acoustic energy emitted from the drumhead. When two energy sources are provided with the apparatus, the acoustic sensor may be positioned between the two energy sources. In certain embodiments, such as the embodiment illustrated in the figures, it may be desirable to position the two energy sources and the acoustic sensor substantially on a single circumferential line located between a center of the drumhead and an outer periphery of the drumhead. In addition, or alternatively, the acoustic sensor may be positioned substantially along a straight line extending from the center of the drumhead through a tightening bolt-lug nut pair, such as the bolt-nut pair containing a tension adjusting device, such as a tension adjusting key or wrench. As discussed herein, drums typically have a plurality of tightening bolt-lug nut pairs located around the perimeter of the drum. These tightening bolts and lug nuts are used to adjust the tension of the drumhead. Thus, the apparatus may measure the acoustic properties of the drumhead by measuring the acoustic properties of the drumhead at multiple locations of the drumhead surface. For example, the acoustic properties may be measured at a location between the center of the drumhead and each of the tightening bolt-lug nut pairs.

The acoustic sensor of the apparatus may comprise, consist essentially of, or consist of, a microphone, but the acoustic sensor may include any device or method that detects the amplitude of the drumhead's vibration without altering the amplitude of the vibration. In some embodiments, a laser may be employed to detect the drumhead vibration. In one embodiment, the microphone is structured to convert acoustic energy into an electrical signal. Such an electrical signal can then be measured by a meter. For example, the microphone may convert the acoustic energy into a voltage. The voltage will typically have an amplitude, and the amplitude of the voltage will typically correspond to the amplitude of the acoustic energy emitted from the drumhead, which directly correlates to the drumhead vibration at that location. The voltage signal may also have a phase that corresponds to the phase of acoustic energy emitted from the drumhead. In certain embodiments, the meter is a separate element coupled to the microphone, and in other embodiments, the meter is provided as an element of the microphone. In other words, the meter may be located away from the microphone or may be located in a microphone housing.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Figure 1:
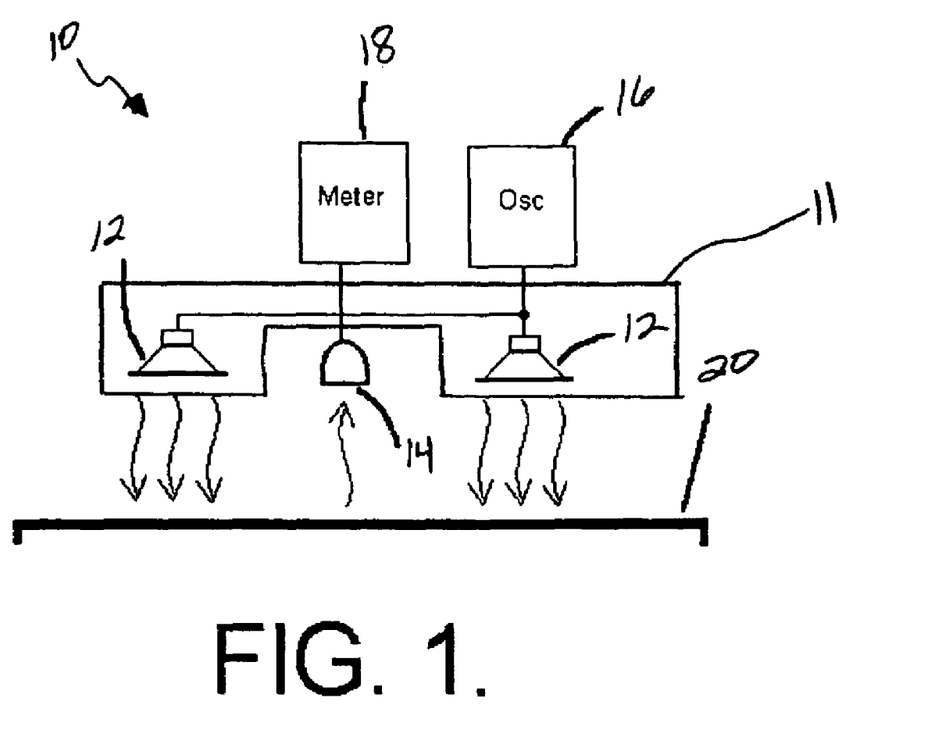
FIG. 1. is a schematic illustration of an apparatus for measuring acoustic properties of a drumhead.

Referring to FIG. 1, an apparatus 10 includes an acoustic energy source 11, such as a plurality of loudspeakers 12, an acoustic sensor 14, such as a microphone or other device having a pressure transducer, a signal source 16 coupled to the loudspeakers 12, and a meter 18 coupled to the acoustic sensor 14. The apparatus is illustrated as being positioned over a drumhead 20 of a drum, which includes any conventional drum used to make music and the like. In the illustrated embodiment, the signal source 16 creates an electrical signal and directs it to loudspeakers 12. The loudspeakers 12 convert the electrical signal received from the signal source 16 to acoustic energy. When the loudspeakers 12 are closely positioned near the drumhead 20, the drumhead 20 will be excited by the energy coming from the loudspeakers 12 and the drumhead 20 will vibrate. The amplitude of this vibration at different frequencies will vary with the amount of energy introduced by the loudspeakers 12 and resonance or tuning of the drumhead 20 caused by the tension of the drumhead 20.

A microphone 14 is located in relatively close proximity to the vibrating drumhead 20. The microphone 14 is positioned to detect the sound (acoustic energy) generated by the vibrating drumhead 20 and convert it to an electric signal, such as a voltage. This voltage will be representative of the amplitude of the drumhead's 20 vibration. The voltage from microphone 14 is measured and displayed by meter 18. Thus, the meter 18 may be a volt meter. The meter may display the value as volts, such as milli-volts, or decibels. The measurement units should be consistent for each of the measurements to facilitate comparison between relative maximum values. By varying the frequency of the exciting signal coming from the loudspeakers 12 while monitoring the meter 18 for voltage amplitude peaks, the resonant frequencies or tuning of the drumhead 20 can be directly detected. In addition, the apparatus may include one or more digital components, such as a microprocessor. In such embodiments, the apparatus may be configured to assist a user by indicating how much adjustment is needed to tune the drumhead, for example, the apparatus may be able to indicate what direction and how far a drum key should be turned when adjusting a drumhead.

Thus, in reference to FIG. 1, an apparatus for measuring acoustic properties of a drumhead comprises an acoustic energy source positioned relative to the drum to provide acoustic energy to the drumhead, and an acoustic energy sensor positioned relative to the drumhead to receive acoustic energy emitted from the drumhead. The acoustic energy sensor is configured to generate an output signal corresponding to the acoustic energy received by the acoustic sensor. The output signal is read by a meter which can then display a value corresponding to the acoustic properties of the drumhead to a subject measuring the acoustic properties.

As shown in FIG. 1, the acoustic energy source 11 comprises a plurality of acoustic drivers or loudspeakers 12; however, in other embodiments, a single speaker may be provided. Although the illustrated embodiment of the apparatus 10 comprises one acoustic sensor 14, additional embodiments may comprise two or more acoustic sensors. When the apparatus comprises two or more acoustic sensors, the sensors may be provided in a single housing, or may be provided as separate elements spaced apart from each other. In addition, shielding or other isolation type devices may be utilized to reduce cross-talk between the various signals.

Figure 1A:
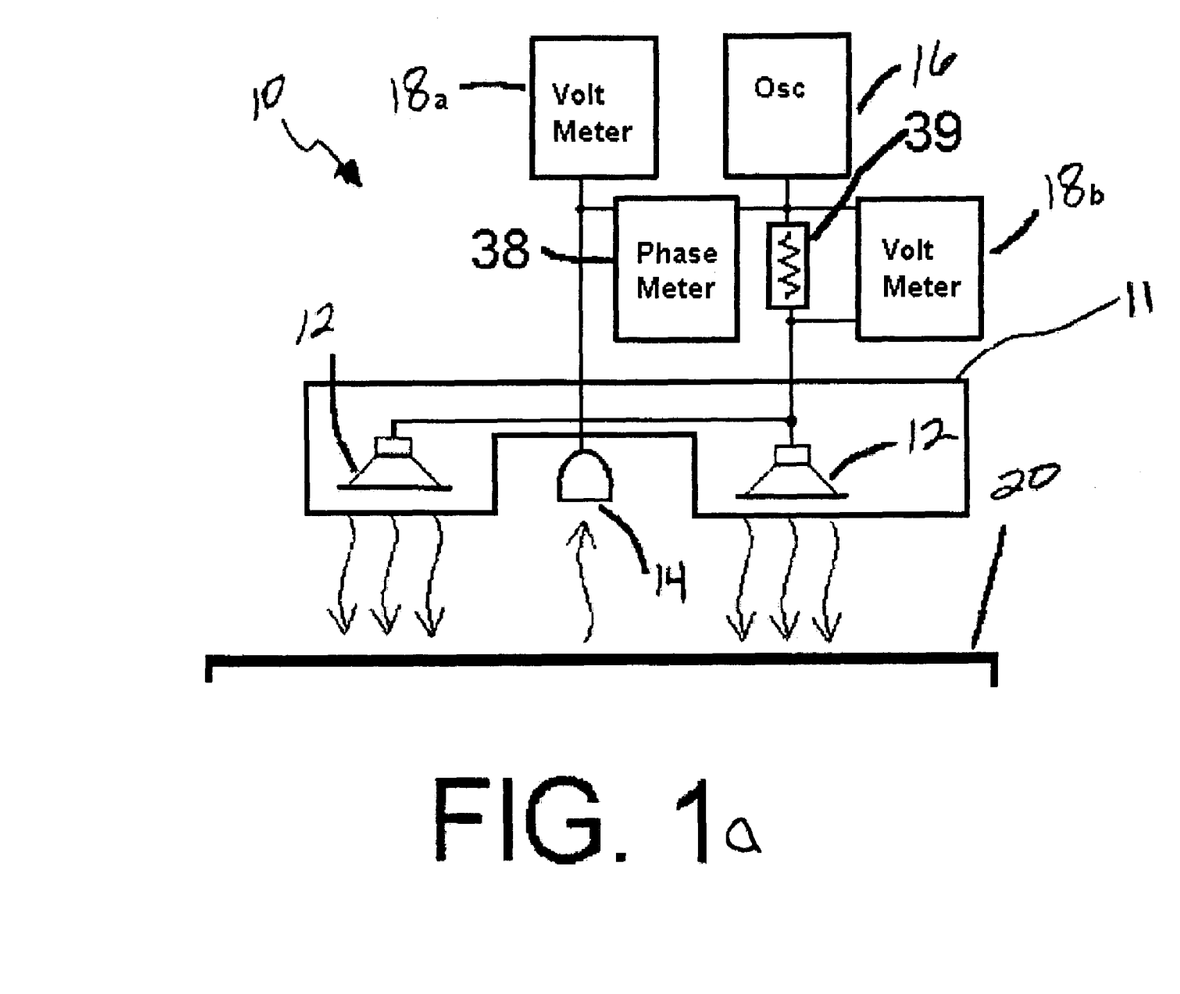
FIG. 1a. is a schematic illustration of an apparatus for measuring additional acoustic properties of a drumhead compared to the drumhead of FIG. 1.

Referring to FIG. 1a, an apparatus 10 is shown with additional measurement or detection devices 18b, 38, and 39 connected to the acoustic sensor 14, a first volt meter 18a, and an electrical input to the loudspeakers 12. The apparatus 10 may include all of these measurement devices or less than all of the measurement devices. The measurement devices 18b, 38, and 39 are provided to evaluate other characteristics (e.g., other than voltage amplitude) of the associated signals which are also representative of the resonant properties or tuning status of drumhead 20. For example, phase meter 38 may be connected between the microphone 14 and oscillator 16 to capture a phase relationship between the exciting signal used to drive the loudspeakers 12 and the vibrating drumhead 20. The phase relationship varies with the resonance or tuning of drumhead 20. A second volt meter 18b is shown connected to the endpoints of a resistive element 39 which is shown as being placed in series between oscillator 16 and loudspeakers 12. Acoustic coupling between drumhead 20 and loudspeakers 12 will cause changes in the tuning or resonant status of drumhead 20 to appear as a variation in the load seen by loudspeakers 12. Voltmeter 18b is configured to measure the voltage drop across resistive element 39. The voltage drop includes information indicative of the resonance or tuning of drumhead 20. Thus, in the embodiment illustrated in FIG. 1a, the apparatus includes an energy sensor that is configured to detect power delivered to the loudspeakers 12. One or more of the meters may provide a signal or information corresponding to the acoustic properties of the drumhead 20.

The components of the apparatus 10 may be any conventional components that are publicly available. For example, the loudspeakers 12 could be 102MM 8 Ohm such as Digi-KeyGF-1004-ND, DigiKey corp., (Thief River Falls, Minn.); the microphone 14 could be Digi-Key P9931-ND; the volt meter 18 could be Fluke 187 Digital Multimeter, the signal source 16 could be B&K Precision 4010A function generator, the resistive element 39 could be a 100 Ohm ¼ Watt resistor such as manufactured by Allen Bradley, and phase meter 38 could be a Clarke-hess model 6000 phase meter, Clark-hess Communication Research corp, (Long Island City, N.Y.). The components of the apparatus 10 may be coupled together using conventional techniques. For example, copper wires and the like, which are capable of transmitting electrical signals, may be used to couple the signal source 16 to the acoustic energy source 11, and to couple the acoustic sensor 14 to the meter 18. Alternatively, or in addition, wireless communication paths may be used to transmit some of the signals. The components may also be coupled together so that two or more of the components are fixed with respect to each other or to the other components. In other words, the components of the apparatus may be provided on a frame or in a housing, thereby forming a unitary apparatus for measuring the acoustic properties of a drum. The apparatus may be portable and positioned about the drum head as needed or substantially fixed in position and the drum moved relative to it.

Figure 2:
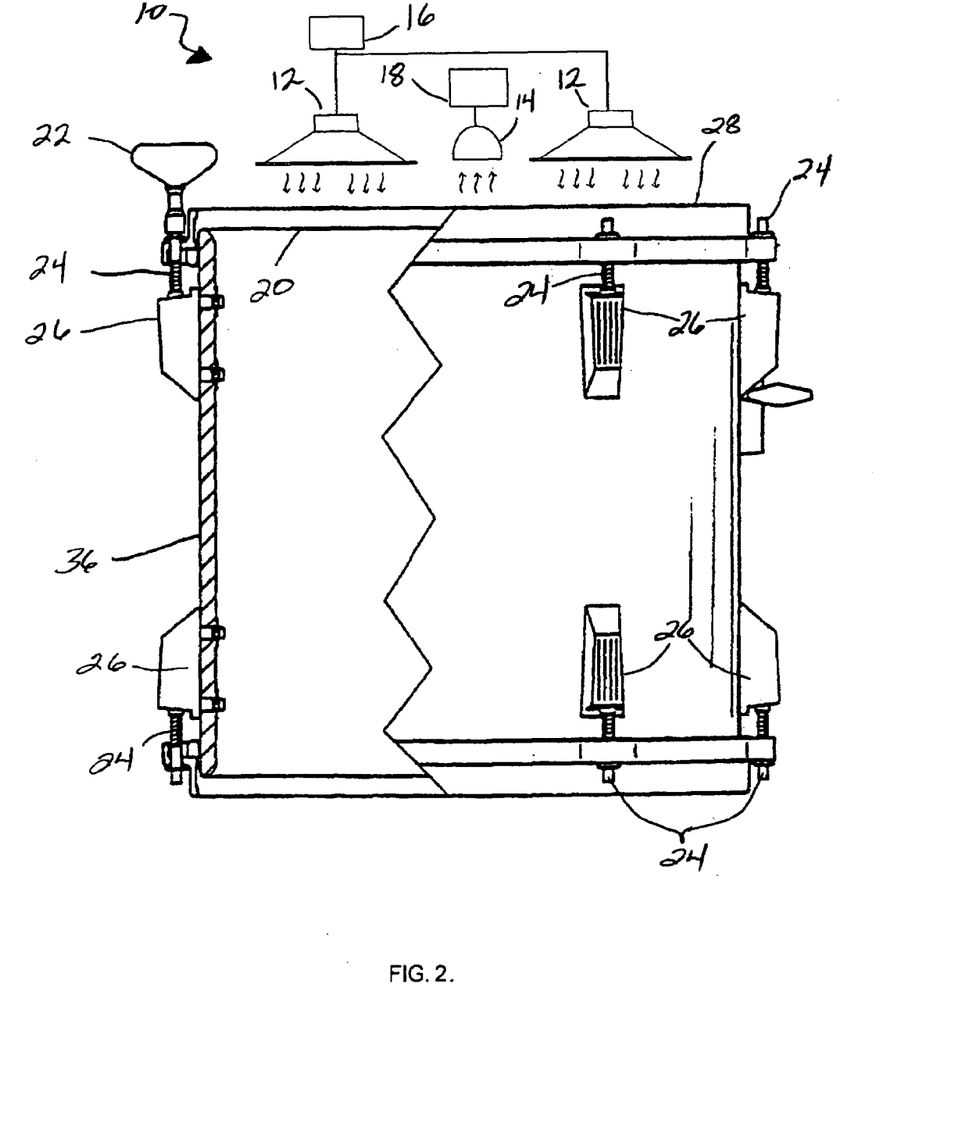
FIG. 2 is a partial sectional side view of a typical drum and the apparatus of FIG. 1.

Referring to FIG. 2, the components of the invention are shown positioned relative to a conventional drum 36. The drumhead 20 vibrates in response to sound coming from the speakers 12. Microphone 14 receives or detects the sound radiated by drumhead 20 and measures this sound with meter 18. A tension adjustment device, such as a drum key 22, is illustrated as being coupled to a tightening bolt 24/lug nut 26 combination or pair. As discussed herein, drums typically have multiple bolt/lug nut pairs disposed around the perimeter of the drum. A drum key, such as drum key 22, is typically placed over the bolt/nut pair to adjust the tension of the drumhead 20. Turning drum key 22 or other suitable tension adjustment device will either increase or decrease the tension of the drumhead 20 at an area adjacent or in proximity to the individual bolt 24/lug nut 26 pair in which the key is placed depending upon direction of rotation. The combined tension from multiple bolt 24/lug nut 26 pairs spaced circumferentially around the drum is converted by the drumhead tensioning ring 28 to a pressure applied evenly to the entire drumhead 20 circumference or surface. The frequencies at which the drumhead will resonate can be tuned by changing the tension of the drumhead 20 while monitoring the output value at the meter 18. The distance of the apparatus 10 above drumhead 20 should be close to the surface of the drumhead but not touching the drumhead. A sufficient amount of clearance should be provided for the unobstructed vibration of drumhead 20. Properly tuned drums are highly resonant at the frequencies being measured so only modest amounts of power, typically less than 2 watts is needed at loudspeaker(s) 12 to provide measurable drumhead 20 vibration. The signal source 16 may generate a sine wave swept from below to above the desired tuning frequency using the loudspeakers 12 to excite the drumhead 20 while monitoring the response on meter 18 for where frequency maxima occur. The results of this test can be used to directly make adjustments to tightening bolt 24/lug nut 26 sets. Or, the signal source 16 could be set to deliver a fixed target tuning frequency and the tightening bolt 24/lug nut 26 adjusted while monitoring the meter 18 for maxima. For good results the assembly 10 components are preferably oriented as shown in FIG. 3, and then the test repeated for each tightening bolt 24/lug nut 26 set as shown in FIG. 4.

Figure 3:
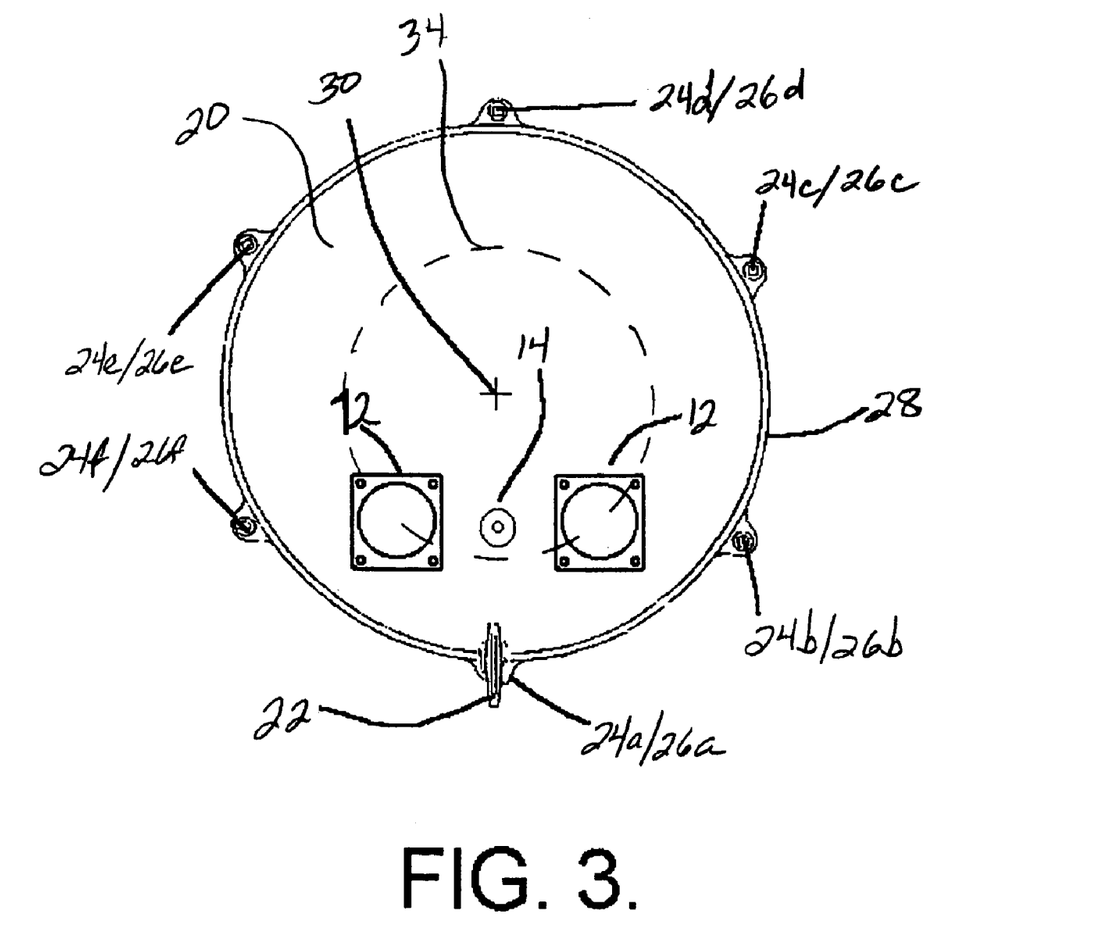
FIG. 3. is a top plan view of the drum and apparatus of FIG. 2.
Figure 3A:
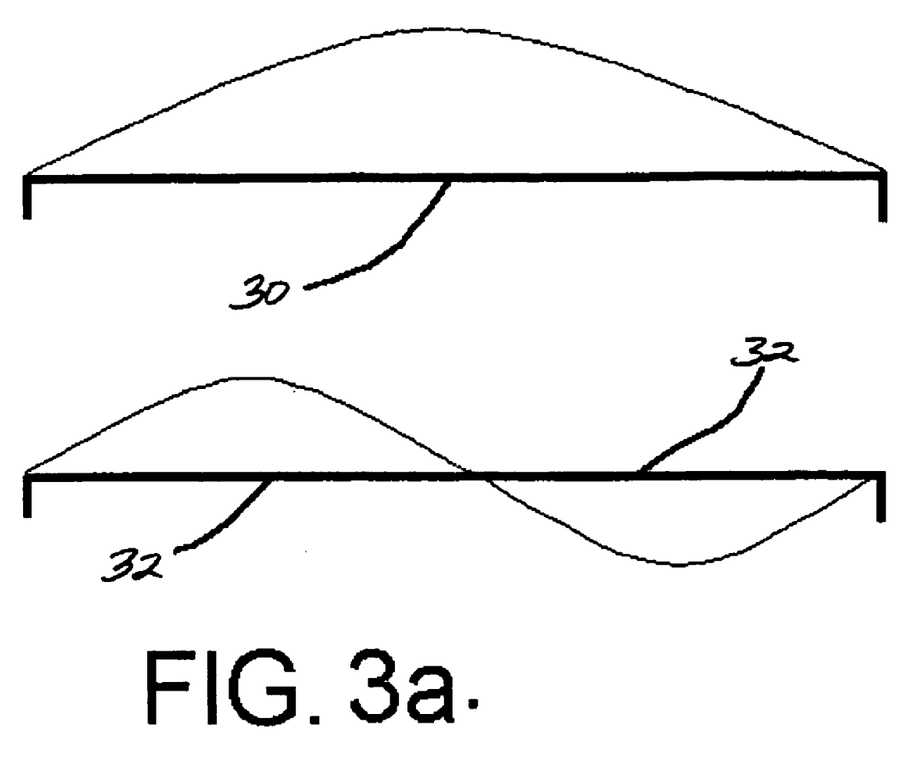
FIG. 3a. side view of a drumhead showing two vibration modes.
Figure 4:
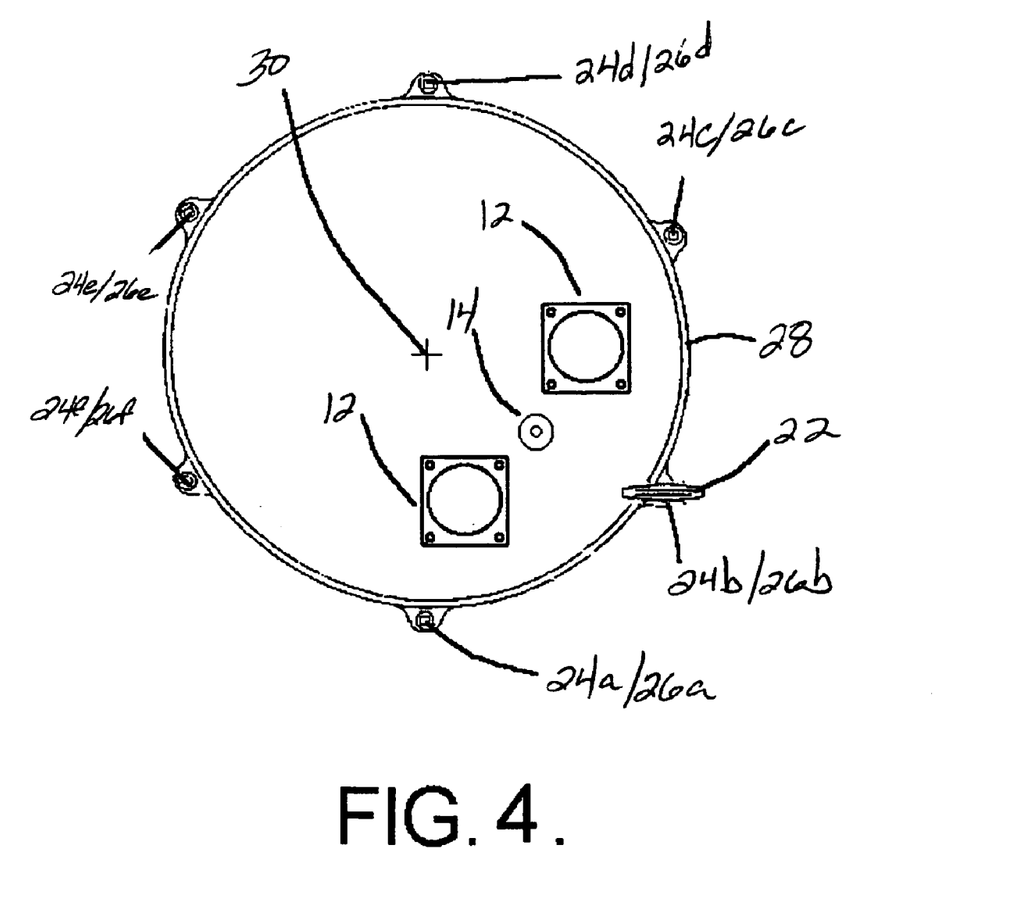
FIG. 4. is a top plan view similar to FIG. 3 illustrating the components of the apparatus in a different position.

Referring to FIG. 3, the components of the invention are shown positioned relative to a typical drum in a top plan view. This view shows the relative location of microphone 14 and loudspeakers 12 with respect to a specific tightening bolt 24a/lug nut 26a pair to increase, and preferably maximize, sensitivity for tuning. The microphone 14 is illustrated as being located halfway from the center 30 of the drumhead 20 to the drumhead's peripheral edge (shown by the position of the tension ring 28). Positioning the microphone 14 equidistantly from the center 30 to the drumhead peripheral edge will attempt to make the microphone less responsive to the primary resonance which is maximum at the drumhead center 30, as shown in the top illustration of FIG. 3a. In addition, positioning the microphone 14 halfway from the center 30 to the drumhead peripheral edge will help make the microphone more responsive to the upper overtone which is maximum at the halfway point 32, as indicated in the lower illustration of FIG. 3a.

Locating multiple speakers 12 over the drumhead 20 as shown in FIG. 3 enables the sound source to be coupled to the drumhead 20 while reducing or attenuating the effect of tension variations of the drumhead 20 associated with the other tightening bolt/lug nut pairs (e.g., the tightening bolt/lug nut pairs that are not being adjusted by lug wrench 22), such as pairs 24b/26b, 24c/26c, 24d/26d, 24e/26e, and 24f/26f, on the measured resonance at microphone 14, thereby effectively allowing the tension of the drumhead 20 in an area closest to bolt 24a/lug nut 26a to be set with lug wrench 22 without significant interference from the other bolt/lug nut pairs. Adjustments to the drumhead 20 may be repeated by repositioning the microphone 14 and speakers 12 in a similar orientation for the other tightening bolt/lug nut pairs until all tightening bolt/lug nut pairs are properly adjusted. For example, FIG. 4. illustrates the position of the loudspeakers 12 and the microphone 14 when the tightening bolt 24b/lug nut 26b pair is being adjusted. Depending on the particular embodiment, the apparatus 10 may be rotated around a circumferential line or axis, such as the circumferential line 34 illustrated in FIG. 3 until the desired acoustic properties are obtained. Or, the drum may be rotated with respect to the apparatus 10 until the desired acoustic properties are obtained. As shown in FIG. 3, the two speakers 12 and the microphone 14 are substantially aligned along a circumferential axis 34. The microphone 14 is typically placed at an approximate midpoint between the speakers 12. In addition, or alternatively, the microphone 14 may be spaced at an approximate midpoint between the center 30 and the peripheral edge of the drumhead 20, as discussed herein. Although the illustrated embodiment shown in FIG. 3 reflects that the microphone 14 is not precisely aligned along the circumferential axis 34, it is understood that in certain embodiments, the microphone or acoustic sensor and the speakers are aligned along a single circumferential axis. Minor deviation from ideal location of these components will affect the amplitude of vibration measured but will not alter the frequency where maximas occur, providing accurate tuning over a range of proximate location.

In view of the above, a method for measuring the acoustic properties of a drumhead comprises applying energy to a surface of the drumhead to cause the drumhead to emit acoustic energy therefrom. The energy may be applied by a mechanical energy source, or an acoustic energy source, as described herein. For example, the energy may be applied by a piston or the like physically contact the drumhead, or the energy may be applied by a speaker that is spaced apart from the surface of the drumhead. The acoustic energy emitted from the drumhead may be received by an acoustic sensor, such as a microphone or other device having a pressure transducer. The acoustic energy that is received by the acoustic sensor may then be converted into a signal that corresponds to the acoustic property of the drumhead, such as an electric signal that can be interpreted by a meter. For example, a microphone may receive the acoustic energy, and the acoustic energy may be converted into a voltage having an amplitude corresponding to the amplitude of the acoustic energy. The value corresponding to the acoustic property of the drum may be displayed by the meter to indicate the acoustic property of the drumhead.

In addition to the primary amplitude relationship described in the illustrated embodiment, additional relationships exist between the signals and means in the examples that contain information related to the tuning status or resonance of the drumhead, as discussed herein. While detecting the amplitude of acoustic energy radiated from the excited drumhead may be preferred, the phase relationship between the exciting and detected signals varies predictably with drumhead tuning and the phase relationship may be a useful measure for determining the acoustic properties of the drumhead. Also acoustic coupling between the drumhead and a closely located driven loudspeaker causes measurable changes in the loudspeaker's current consumption that correlates with drumhead tuning. These additional relationships can be used alone or in combination with the illustrated embodiment to extract useful information about the drum tuning.

Thus, these and other modifications and additions may be obvious to those skilled in the art and may be implemented to adapt the present invention for use in a variety of different applications. While this invention has been described with respect to various specific examples and embodiments, it is to be understood that the invention is not limited thereto and that it can be variously practiced with the scope of the following claims. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims. It is anticipated that advances in digital signal processing would allow this and other information about drumheads to be computed from variations on techniques taught by this application. Some of the decisions and interpretation made by the user in this basic invention could be supplanted by portable electronic computational power.

What is claimed is:

1. An apparatus for measuring acoustic properties of a drumhead of a drum, the apparatus comprising:
   a) a moveable acoustic source positioned relative to the drum to provide acoustic energy to the drumhead; and
   b) a moveable acoustic energy sensor positioned above the drumhead to receive acoustic energy produced from the drumhead at an area in proximity to a tightening bolt of the drum without substantial interference from other tightening bolts of the drum and configured to generate an output corresponding to the acoustic energy received by the acoustic sensor, the output effective in permitting the tuning of each tightening bolt of the drum to be matched to the other tightening bolts of the drum.

2. The apparatus as recited in claim 1, wherein the acoustic source comprises a speaker to provide acoustic energy to the drumhead.

3. The apparatus as recited in claim 1, wherein the acoustic energy sensor comprises a microphone.

4. The apparatus as recited in claim 1, wherein the apparatus comprises a plurality of acoustic sources positioned relative to the acoustic energy sensor to provide acoustic energy to the drumhead and to provide a controlled environment for making local measurements.

5. The apparatus as recited in claim 4, wherein the acoustic sources comprise a plurality of speakers.

6. The apparatus as recited in claim 4, wherein the acoustic energy sensor comprises a microphone.

7. The apparatus as recited in claim 4, wherein the acoustic energy sensor comprises a plurality of microphones.

8. The apparatus as recited in claim 4, wherein the plurality of acoustic sources are spaced apart along a circumferential axis of the drumhead and the acoustic sensor is located substantially equidistant from the plurality of acoustic sources along the circumferential axis.

9. The apparatus as recited in claim 1, wherein the acoustic source comprises a plurality of speakers configured to direct acoustic energy towards the drumhead, wherein the acoustic sensor comprises a microphone located between the plurality of speakers, and further comprising an acoustic energy source coupled to the plurality of speakers, and a meter coupled to the microphone, the meter being configured to provide a measurement of the acoustic properties of the drumhead.

10. An apparatus for measuring acoustic properties of a drumhead of a drum, the apparatus comprising:
- a moveable energy source positioned relative to the drum to cause the drumhead to vibrate when energy is delivered from the energy source towards the drumhead; and
- a moveable acoustic sensor positioned above the drumhead at an area in proximity to a tightening bolt of the drum to receive acoustic energy therefrom without substantial interference from other tightening bolts of the drum, and coupled to a meter configured to display information corresponding to the acoustic properties of the drumhead and permitting the adjustment of each tightening bolt of the drum to a single resonant frequency.

11. The apparatus as recited in claim 10, wherein the energy source comprises an acoustic energy source coupled to at least one speaker configured to emit acoustic energy.

12. The apparatus as recited in claim 10, wherein the energy source is spaced away from the drumhead.

13. The apparatus as recited in claim 10, wherein the acoustic sensor comprises a microphone structured to convert acoustic energy into an electrical signal measurable by the meter.

14. The apparatus as recited in claim 13, wherein the microphone is structured to convert acoustic energy into a voltage having an amplitude, the amplitude of the voltage corresponding to the amplitude of the acoustic energy emitted from the drumhead.

15. The apparatus as recited in claim 10, wherein the apparatus comprises two energy sources spaced apart by a distance, and wherein the acoustic sensor is positioned between the two energy sources.

16. The apparatus as recited in claim 15, wherein the two energy sources and the acoustic sensor are located substantially on a single circumferential line positioned between a center of the drumhead and an outer periphery of the drumhead.

17. The apparatus as recited in claim 16, wherein the drum includes a plurality of tension bolt-lug nut pairs located around a periphery of the drum, and a tension adjusting device located in one of the tension bolt-lug nut pairs, and wherein the acoustic sensor is positioned substantially along a straight line extending from a center point of the drumhead through the tension bolt-lug nut pair containing the tension adjusting device.

18. A method for measuring the acoustic properties of a drumhead of a drum, comprising:
- applying energy to a surface of the drumhead to cause the drumhead to emit acoustic energy therefrom;
- receiving acoustic energy emitted from the drumhead using moveable acoustic sensor positioned above the surface of the drumhead and in proximity to a tightening bolt of the drum without substantial interference from other tightening bolts of the drum;
- converting the acoustic energy received by the acoustic sensor into a signal corresponding to an acoustic property of the drumhead; and
- adjusting all of the tightening bolts of the drum to a single resonant frequency.

19. The method as recited in claim 18, wherein the energy applied to the surface of the drumhead comprises acoustic energy emitted from a speaker spaced apart from the surface of the drumhead.

20. The method as recited in claim 18, wherein the acoustic sensor comprises a microphone, and wherein the acoustic energy received from the microphone is converted into a voltage having an amplitude corresponding to the amplitude of the acoustic energy, and further comprising displaying a value corresponding to the amplitude of the voltage.

21. An apparatus for measuring acoustic properties of a drumhead of a drum, the apparatus comprising:
- a moveable loudspeaker positioned relative to the drum to cause the drumhead to vibrate when energy is delivered from the loudspeaker towards the drumhead; and
- an electrical energy sensor that detects power delivered to the loudspeaker, is located above the drumhead in proximity to a tightening bolt of the drum to receive acoustic energy therefrom without substantial interference from other tightening bolts of the drum, and is coupled to a meter configured to display information corresponding to the acoustic properties of the drumhead to permit the tuning of each tightening bolt of the drum to be matched to the other tightening bolts of the drum.

* * * * *